United States Patent
Timmis et al.

(10) Patent No.: US 7,977,375 B2
(45) Date of Patent: Jul. 12, 2011

(54) ANTIBIOTIC AND METHOD OF PRODUCTION THEREOF

(75) Inventors: Kenneth N. Timmis, Wolfenbüttel (DE); Gabriella Molinari, Wolfenbüttel (DE); Rolf Jansen, Braunschweig (DE); Magally Romero-Tabarez, Braunschweig (DE); Dwi Andreas Santosa, Bogor (ID)

(73) Assignee: Helmholtz-Zentrum Für Infektionsforschung GmbH, Braunschweig (DE)

( * ) Notice: Subject to any disclaimer, the term of this patent is extended or adjusted under 35 U.S.C. 154(b) by 867 days.

(21) Appl. No.: 11/663,408

(22) PCT Filed: Sep. 21, 2005

(86) PCT No.: PCT/EP2005/054736
§ 371 (c)(1),
(2), (4) Date: Jul. 20, 2007

(87) PCT Pub. No.: WO2006/032683
PCT Pub. Date: Mar. 30, 2006

(65) Prior Publication Data
US 2008/0039407 A1    Feb. 14, 2008

(30) Foreign Application Priority Data
Sep. 21, 2004 (DE) .................. 10 2004 046 024

(51) Int. Cl.
*A61K 31/335* (2006.01)
*C07D 305/00* (2006.01)

(52) U.S. Cl. ........................ 514/450; 549/263

(58) Field of Classification Search ................. None
See application file for complete search history.

(56) References Cited

FOREIGN PATENT DOCUMENTS
JP    9301970    11/1997

OTHER PUBLICATIONS

International Search Report.
Jaruchoktaweechai, Chutima et al., "New Macrolactins from a Marine *Bacillus* sp. Sc026", *Journal of Natural Products*, 2000, pp. 984-986. XP-002352574.
Smith, Amos B. et al., "Total Synthesis of (−)-Macrolactin A", *Journal of the American Chemical Society*, vol. 118, 1996, pp. 13095-13096. XP-002207324.
Smith, Amos B. et al., "Total Synthesis of (−)-Macrolactin A, (+)-Macrolactin E, and (−)-Macrolactinic Acid: An Exercise in Stille Cross-Coupling Chemistry", *Journal of the American Chemical Society*, vol. 120, 1998, pp. 3925-3948. XP-002352575. (Spec, p. 2).
Marino, Joseph P. et al., "Stereocontrolled Synthesis of (−)-Macrolactin A", *Journal of the American Chemical Society*, vol. 124, No. 8, 2002, pp. 1664-1668. XP-002352576. (Spec, p. 2).

*Primary Examiner* — Elli Peselev
(74) *Attorney, Agent, or Firm* — Greer, Burns & Crain Ltd.

(57) ABSTRACT

The invention relates to a novel antibiotic from the macrolactin group and a microbial method for production of macrolactins and a novel isolated *Bacillus subtilis*, of application as the producing strain for the known Macrolactin A and the novel derivative.

6 Claims, 7 Drawing Sheets

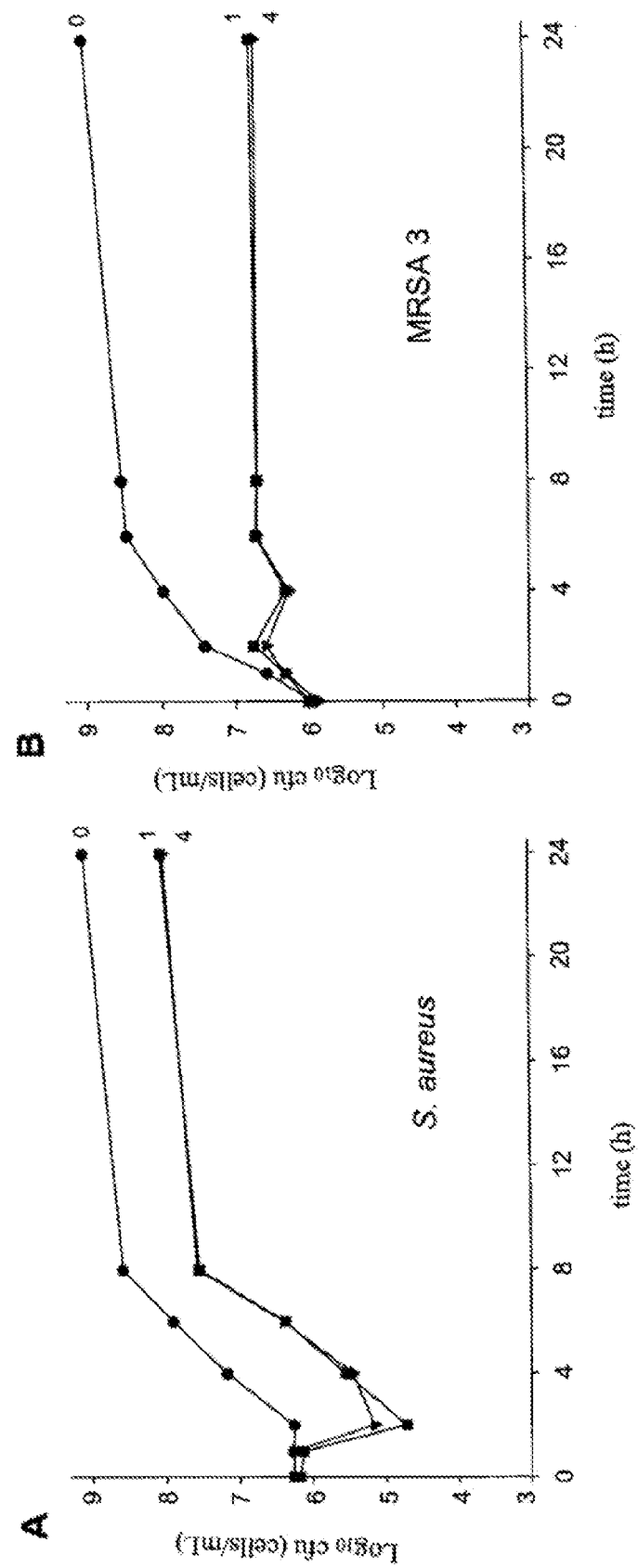

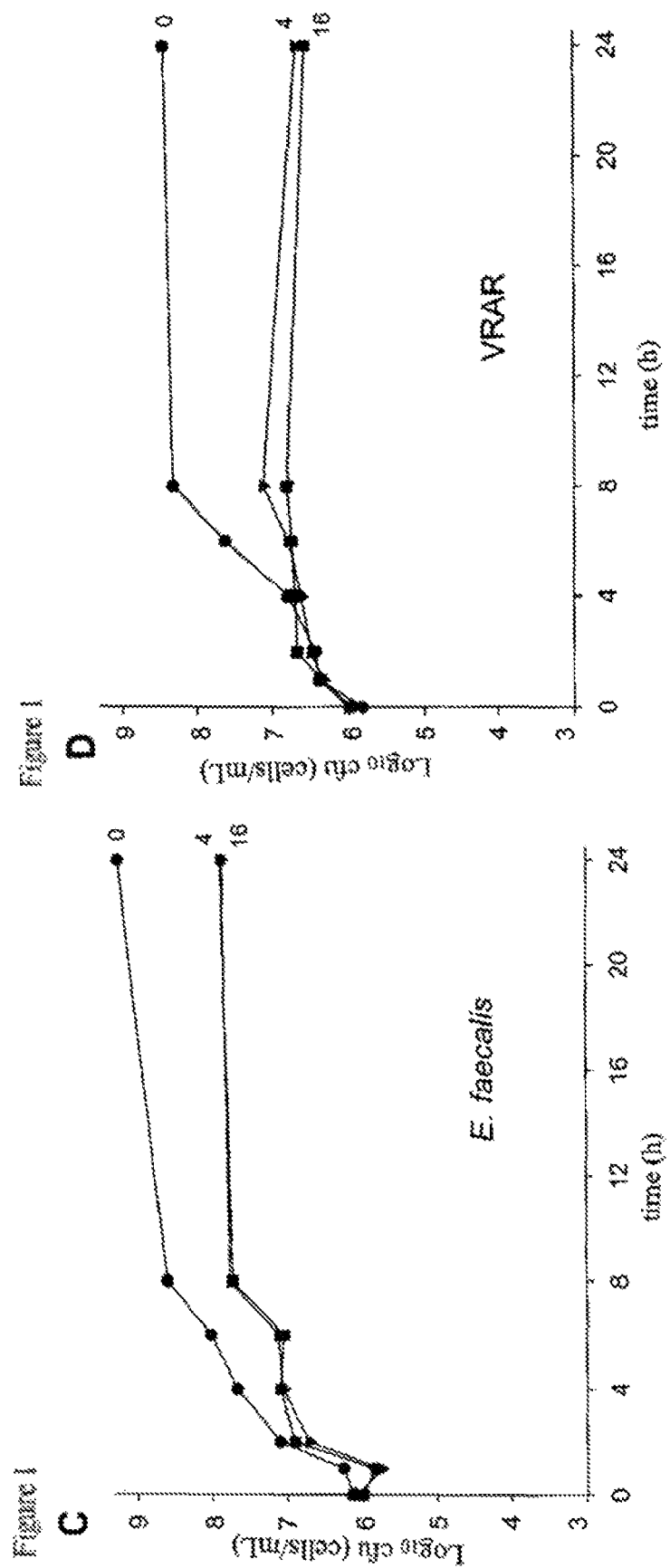

ANTIBIOTIC AND METHOD OF PRODUCTION THEREOF

CROSS REFERENCE TO RELATED APPLICATIONS

Applicants claim priority under 35 U.S.C. §119 of German Application No. 10 2004 046 024.8 filed Sep. 21, 2004. Applicants also claim priority under 35 U.S.C. §365 of PCT/EP2005/054736 filed Sep. 21, 2005. The international application under PCT article 21(2) was not published in English.

The present invention relates to a novel antibiotic of the macrolactin family as well as to a microbial method suitable for producing macrolactins and the producer strain thereof.

It is acknowledged that bacteria, more particularly pathogenic bacteria, are becoming increasingly resistant to known antibiotics. An example of this phenomenon are staphylococci which, being a cause of nosocomial infections, are also resistant to methicillin and other known antibiotics with the exception of vancomycin and teicoplanin. Emerging in recent years, however, have been staphylococcal strains that are resistant to vancomycin or to the precursors thereof.

The object of the present invention is, therefore, the preparation of novel, medically effectual substances, more particularly those, which, having antibacterial activity, can be used as an antibiotic against bacterial and/or eurkaryotic infections.

A further object of the present invention is a method for producing substances suitable for pharmaceutical use, an example whereof are antibiotically active substances, and a bacterium that can be employed by the method as a producer of antibiotic substances.

THE STATE OF THE ART

Known in the art are several macrolactins that include macrolactin A of the chemical formula 8, 14, 16-trihydroxy-24(R)-methyl-oxacyclotetracosa-3(Z), 5(B), 9(E), 11(Z), 17(E), 19(E)-hexaen-2-on. Macrolactin A, which is known to be antiviral and for example, is active against HIV, is cytotoxic. The antibacterial activity of macrolactin A is, on the other hand, relatively weak.

JP 9301970 discloses that the derivative macrolactin M is antimicrobially active.

Methods for chemically synthesizing macrolactin A are disclosed in Smith et al., *J. Am. Chem. Soc*, 120, 3935-3948 (1998) and in Marino et al., *J. Am. Chem. Soc*. 124, 8, 1664-1668 (2002).

OVERVIEW OF THE INVENTION

7-O-malonyl macrolactin A is, first of all, highly effective against bacteria and can thus confer antibiotic capability on pharmaceutical compositions. In addition, 7-O-malonyl macrolactin A at low concentrations is less cytotoxic than macrolactin A and is, therefore, especially suitable for use in pharmaceutical compositions.

In addition to its general antibacterial effectiveness, 7-O-malonyl macrolactin A is antibiotically active against at least some bacteria that exhibit resistance to known antibiotics or are in and of themselves resistant. In this regard, 7-O-malonyl macrolactin A interestingly enough exhibits, at concentrations below the minimal inhibitory concentration level, strong bacteriostatic activity against at least a number of bacteria from clinical isolates that are resistant to conventional antibiotics, as opposed to the corresponding non-resistant strains. For example, 7-O-malonyl macrolactin A is antibiotically effective against both methicillin-resistant *Staphylococcus aureus* and vancomycin and ampicillin-resistant *Enterococcus faecium*.

The structural formula for 7-O-malonyl macrolactin A is reproduced hereunder:

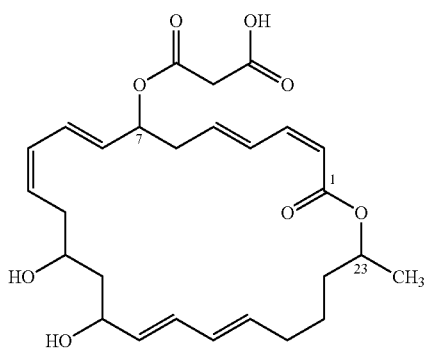

The proposed compounds, which are suitable for use as active ingredients in pharmaceutical products, are produced from a strain of *Bacillus subtilis* that was deposited with the Indonesian Center for Biodiversity and Biotechnology under No. ICBB 1582 (also deposited under no. DSM 16696 with the DSMZ, Mascheroder Weg 1, 38124 Braunschweig, date of filing Sep. 6, 2004). This strain was isolated from a soil sample obtained in Takalar, South Sulawesi in Indonesia.

The deposited producer strain was characterized as a gram-positive rod (±0.2 μm diameter) capable of motility by means of flagella, forming endospores and in culture (5 g/l yeast extract, 20 g/l tryptone, 5 g/l sodium chloride, 20 g/l glucose, 15 g/l agar) forming opaque, milky-white colonies exhibiting undulating, rough edges. In the API system (Biomerieux), positive reactions were observed for the following: oxidase, ornithine, mannitol, Voges-Proskauer, citrate, TDA and amylohydrolysis, whereas negative reactions were observed for nitrate, lysine, hydrogen sulfide production, glucose, xylose, β-galactosidase, indol and urease. Following the biochemical tests and the homology test of the 16S-RNA sequence searches using the FASTA program, the strain was determined to be *Bacillus subtilis*.

The present invention also relates to a method employing fermentation for producing the prior art macrolactin A, 7-O-succinyl macrolactin A and 7-O-malonyl macrolactin A.

The present invention relates furthermore to the application of 7-O-succinyl macrolactin A to the production of pharmaceutical preparations for medical use in combating antibiotic-resistant, e.g. multiresistant bacteria.

It is therefore proposed that pharmaceutical compositions be prepared that comprise at least one of the aforementioned compounds.

DETAILED DESCRIPTION OF THE INVENTION

7-O-Malonyl Macrolactin A

7-O-malonyl macrolactin A is antibiotically active against bacteria, especially gram-positive bacteria and is, in particular, advantageously bacteriostatic at very low concentrations, for example, in the region of 0.05-4 μg/ml. This activity is especially evident against antibiotic-resistant bacteria, which enables 7-O-malonyl macrolactin A to be particularly effective in combating antibiotic-resistant bacteria, including notably gram-positive bacteria, or at least in inhibiting the further proliferation thereof. The bacteriostatic activity of 7-O-malonyl macrolactin A has already been observed at weak concentrations, as compared to the prior art macrolactin A, even where there has been no direct or immediate bactericidal effect at such low concentrations.

Yet another advantage of 7-O-malonyl macrolactin A as compared to prior art 7-O-succinyl macrolactin A or macrolactin A is its bacteriostatic activity against antibiotic-resistant bacteria even at very low concentrations. Such antibiotic-resistant bacteria can, for example, be obtained from clinical isolates and be resistant to erythromycin or vancomycin or be multiresistant, examples whereof are *Staphylococcus aureus* (MRSA) or enterococci (VRE) from clinical samples. In addition to its activity against such gram-positive bacteria, 7-O-malonyl macrolactin A is active against gram-negative bacteria, e.g. small colony-forming variants (SCV) of *Burkholderia cepacia*. The antibacterial activity of 7-O-malonyl macrolactin A against antibiotic-resistant strains and SCV is more pronounced than against wild-type strains. 7-O-malonyl macrolactin A at higher concentrations also inhibits eukaryotic microorganisms such as pathogenic yeasts, especially *Candida krusei*.

Due to its bacteriostatic effectiveness, 7-O-malonyl macrolactin A is preferred for employment in the manufacture of pharmaceutical preparations for use against the following medical conditions: bacterial infections; endocarditis; meningitis; osteomyelitis; included are infections caused by toxin-forming pathogens e.g. streptococci and staphylococci, more particularly, toxic shock syndrome (TSS) strains of *Staphylococcus aureus*.

The proposed compositions can also have application against other medical conditions such as respiratory tract infections caused, in particular, by antibiotic-resistant (e.g. resistant to penicillin) bacteria or bacteria that are difficult to manage with conventional antibiotics, such as, for example, surface-dwelling pathogens. Examples of respiratory tract infections are those caused by extracellular and/or intracellular bacteria, such as, for example, streptococci e.g. *Streptococcus pneumoniae* or *Streptococcus pyogenes*.

The ability of 7-O-malonyl macrolactin A to inhibit bacterial growth at low concentrations that can be significantly below the MIC is medically significant, in particular, against clinically relevant strains, e.g. those that exhibit resistance. 7-O-malonyl macrolactin A, even at low concentrations, interferes with cell division in both gram-positive and gram-negative bacteria A, which is supported by visual evidence of disrupted septum formation and cell wall alterations using an electron microscope. Thus, for example, antibiotic-resistant enterococci, in particular VRE, staphylococci, in particular MRSA, and *Burkholderia cepacia* SCV in the presence of 7-O-malonyl macrolactin A exhibit a thickened cell wall and/or an anomalous morphology. Interruption of cell division leads to pseudomulticellular accumulations incapable of forming daughter cells. It is presently thought that the reduction of the propagation of bacterial infections by means of 7-O-malonyl macrolactin A is also attributable to the disruption of cell division, since the proliferation of the bacteria can thus be retarded or prevented.

7-O-malonyl macrolactin A, which is produced from the *Bacillus subtilis* strain deposited under no. DSM 16696, is precipitated out in the culture broth. 7-O-malonyl macrolactin A, 7-O-succinyl macrolactin A and macrolactin A are extracted from the culture broth by means, for example, of adsorption to a hydrophobic adsorbent resin such as XAD, whereafter said resin is washed with aqueous methanol and eluted with 100% methanol. 7-O-malonyl macrolactin A is then isolated from the resulting eluate.

7-O-Malonyl macrolactin A: $C_{27}H_{36}O_8$, M=488.57, UV (MeOH) $\lambda_{max}$ (lg $\epsilon$)=227 nm (4.397), 230 (sh), 260 (4.006). $[\alpha]^{22}_D$=−6.2 (c=0.63 in MeOH), MS: (−)-ESI (TOF): m/z (%)=487.2 (100) [M−H]$^-$, 443.2 (44) [M−H−$CO_2$]$^-$, 383.2 (27) [M−H-malonic acid]$^-$.

The foregoing compound was identified as a macrolactin type compound from its UV spectrum that was identical to that of macrolactin A. Mass spectrometry indicated a molecular weight of 488, which is 86 absolute mass units higher than the mass observed for macrolactin A. Corresponding to the elimination of one $H_2O$ from macrolactin A, 7-O-malonyl macrolactin A showed the loss of malonic acid by a fragment ion at a m/z of 383 in the (−)-ESI spectrum. The NMR data for 7-O-malonyl macrolactin A, which are shown in Table 1, were nearly identical to those of macrolactin A. However, compared to macrolactin A, the 7-H signal was shifted about 1.2 ppm downfield as a consequence of the acylation of 7-O. The radical bonded to the 7-O was identified by NMR spectroscopy in comparison with macrolactin A. The sole carboxy group was directly visible in the NMR spectra in dichloromethane-$d_4$, and the malonyl residue was clearly indicated by additional carboxy $^{13}C$ signals at 166.33 and 169.15 ppm and a methylene $^{13}C$ signal at 42.17 ppm. The related methylene $^1H$ signals were observed as doublet signals at 3.51 and 3.40 ppm (J=15.5 Hz). Only one carboxy-$^{13}C$— signal was observed in methanol-$d_4$.

TABLE 1

NMR data for macrolactin A and 7-O-malonyl macrolactin A in methanol-$d_4$

| | Macrolactin A | | | | | | 7-O-malonyl macrolactin A | | | | |
|---|---|---|---|---|---|---|---|---|---|---|---|
| H | $\delta_H$ | m | J [Hz] | C | $\delta_C$ | m | H | $\delta_H$ | m | J [Hz] | C | $\delta_C$ |
| 1 | — | — | — | 1 | 168.02 | s | 1 | — | — | — | 1 | 167.94 |
| 2 | 5.58 | d | 11.33 | 2 | 118.00 | d | 2 | 5.59 | d | 11.7 | 2 | 118.52 |
| 3 | 6.67 | t | 11.71 | 3 | 144.96 | d | 3 | 6.67 | t | 11.3 | 3 | 144.50 |
| 4 | 7.26 | dddd | 15.1, 11.4, 2, 1 | 4 | 130.26 | d | 4 | 7.25 | dd | 14.7, 11.7 | 4 | 130.79 |
| 5 | 6.20 | m | — | 5 | 142.16 | d | 5 | 6.15 | dt | 15.4, 7.2 | 5 | 140.51 |
| 6 | 2.45 | m | — | 6 | 42.84 | t | 6 | 2.60 | m | 5.3 | 6 | 40.13 |
| 7 | 4.29 | ddt | 4.9, 1.2, 6.8 | 7 | 72.33 | d | 7 | 5.50 | ddd | 6.0, 6.0, 6.0 | 7 | 74.72 |
| 8 | 5.79 | dd | 15.1, 6.0 | 8 | 137.55 | d | 8 | 5.75 | dd | 15.3, 5.5 | 8 | 132.06 |
| 9 | 6.61 | ddt | 15.2, 11.0, 1.1 | 9 | 125.96 | d | 9 | 6.71 | dd | 15.1, 11.3 | 9 | 128.09 |
| 10 | 6.15 | t | 11.14 | 10 | 131.39 | d | 10 | 6.13 | t | 10.2 | 10 | 130.91 |
| 11 | 5.58 | ddd | 10.5, 8.6, 8.2 | 11 | 128.39 | d | 11 | 5.63 | dt | 10.6, 8.4 | 11 | 129.78 |
| 12a | 2.53 | dddd | 13.5, 8.2, 7.4, 0.8 | 12 | 36.50 | t | 12a | 2.63 | m | — | 12 | 36.39 |
| 12b | 2.36 | dddd | 13.5, 7.7, 4.9, 1.1 | | | | 12b | 2.33 | ddd | 13.0, 7.2, 5.5 | | |
| 13 | 3.89 | ddt | 5.3, 5.1, 6.9 | 13 | 69.24 | d | 13 | 3.84 | ddd | 10.6, 6.0, 5.7 | 13 | 69.51 |

TABLE 1-continued

NMR data for macrolactin A and 7-O-malonyl macrolactin A in methanol-$d_4$

| | Macrolactin A | | | | | | 7-O-malonyl macrolactin A | | | | |
|---|---|---|---|---|---|---|---|---|---|---|---|
| H | $\delta_H$ | m | J [Hz] | C | $\delta_C$ | m | H | $\delta_H$ | m | J [Hz] | C | $\delta_C$ |
| 14 | 1.65 | m | — | 14 | 43.92 | t | 14 | 1.66 | m | — | 14 | 43.84 |
| 15 | 4.34 | dt | 6.3, 6.3 | 15 | 69.83 | d | 15 | 4.39 | dt | 6.3, 6.3 | 15 | 69.77 |
| 16 | 5.60 | dd | 15.1, 6.5 | 16 | 135.23 | d | 16 | 5.60 | dd | 15.1, 6.4 | 16 | 135.32 |
| 17 | 6.21 | dd | 15.5, 10.9 | 17 | 131.21 | d | 17 | 6.21 | dd | 15.1, 10.6 | 17 | 131.27 |
| 18 | 6.09 | dd | 14.9, 10.4 | 18 | 131.72 | d | 18 | 6.10 | dd | 15.1, 10.6 | 18 | 131.78 |
| 19 | 5.69 | ddd | 14.7, 7.2, 6.8 | 19 | 135.13 | d | 19 | 5.69 | ddd | 14.9, 7.0, 6.8 | 19 | 135.10 |
| 20a | 2.23 | ddt | 14.2, 7.1, 6.8 | 20 | 32.98 | t | 20a | 2.23 | td | 14.0, 6.8 | 20 | 33.03 |
| 20b | 2.14 | ddt | 14.2, 6.4, 7.1 | | | | 20b | 2.15 | td | 14.4, 7.2 | | |
| 21 | 1.54 | m | — | 21 | 25.65 | t | 21 | 1.54 | m | — | 21 | 25.81 |
| 22a | 1.68 | m | — | 22 | 36.01 | t | 22a | 1.70 | m | — | 22 | 36.08 |
| 22b | 1.61 | m | — | | | | 22b | 1.62 | m | — | | |
| 23 | 5.05 | ddq | 7.3, 4.5, 6.2 | 23 | 72.21 | d | 23 | 5.05 | ddq | 4.5, 7.1, 6.1 | 23 | 72.37 |
| 24 | 1.29 | d | 6.04 | 24 | 20.11 | q | 24 | 1.30 | d | 6.0 | 24 | 20.14 |
| 1' | — | — | — | — | — | — | 1' | — | — | — | 1' | 169.64 |
| 2' | — | — | — | — | — | — | 2' | 2.90 | m | —(br) | 2' | 44.74 |
| 3' | — | — | — | — | — | — | 3' | — | — | — | 3' | n/o |

$^1$H at 600 MHz; $^{13}$C at 150 MHz; (a) from the HMQC-NMR spectrum.
n/o = not observed due to signal scattering.
The multiplicity of carbon signals were captured from the DEPT and HMQC spectra.

Macrolactin A

Macrolactin A: $C_{24}H_{35}O_5$, M=402.53, UV (Methanol): $\lambda_{max}$ (lg ε)=227 nm (4.537), 261 (4.146) [Lit.: 227 (4.691), 261 (4.272)]. $[\alpha]^{22}_D$=−10.7 (c=0.68 in MeOH) [Lit.: −9.6 [c=1.86 in MeOH]. MS: (−)-ESI (TOF): m/z (%)=401.2 (38) [M−H]$^−$, 437.2 (100) [M+Cl]$^−$, 803.4 (63) [2M−H]$^−$; (−)-DCI (isobutane): m/z (%)=402 (100); (+)-DCI (isobutane): m/z (%)=349 (56) [M+H-3H$_2$O]$^+$, 367 (100); [M+H-2H$_2$O]$^+$, 385 (75) [M+H-2H$_2$O]$^+$; EI (200° C.): m/z (%)=255 (100), 273 (72), 348 (18), 366 (68), 384 (60), 400 (5.9), 402 (2.5). The NMR data are shown in Table 1.

7-O-Succinyl Macrolactin A $C_{28}H_{38}O_8$, M=502.60: UV (MeOH): $\lambda_{max}$ (lg ε)=227 nm (4.596), 259 (4.192) [Lit.: 229 (4.57), 261 (4.18)]. $[\alpha]^{22}_D$=−19.9 (c=0.7 in MeOH) [Lit.: −9.6 [c=0.18 in MeOH]. MS: (−)-ESI (TOF): m/z (%)=501.3 (100) [M−H]$^−$, 117.0 (12) [Bernstein acid-H]$^−$; (−)-DCI (isobutane): m/z (%)=502.7 (100); 484 (44), 402 (18), 384 (68), 366 (26), 117 (20).

The $^1$H NMR data in CDCl$_3$ were found to be identical to those described by Jaruchoktaweechai et al. J. Nat. Prod. 63, (7), 984-986 (2000).

The chemical properties of the three aforementioned macrolactin compounds, which are produced from *Bacillus subtilis* DSM 16696, are summarized in Table 2, which is reproduced hereunder:

Medical Application of 7-O-Succinyl Macrolactin A Against Antibiotic-Resistant Bacteria 7-O-succinyl macrolactin A, like the above-described 7-O-malonyl macrolactin A, exhibits vigorous activity against antibiotic-resistant bacteria, such as, e.g. multiresistant bacteria, and particularly against bacteria which, for example, are resistant to one of a group comprising vancomycin, erythromycin, methicillin or ampicillin.

The present invention therefore also enables the employment of 7-O-succinyl macrolactin A in the manufacture of pharmaceutical preparations that are effective against antibiotic-resistant bacteria. In view of the striking bacteriostatic effectiveness of low concentrations (sub-MIC, i.e. in the region of the MBC) of 7-O-succinyl macrolactin A and of 7-O-malonyl macrolactin A against antibiotic-resistant bacteria, such pharmaceutical preparations can contain 7-O-succinyl macrolactin A and 7-O-malonyl macrolactin A alone or in combination. The combination of 7-O-succinyl macrolactin A with 7-O-malonyl macrolactin A is especially preferred, since each can be bacteriostatically active against specific antibiotic-resistant bacteria.

Production Method Using Fermentation

The proposed *B. subtilis* DSM 16696 strain can be used in the production of 7-O-malonyl macrolactin A, 7-O-succinyl macrolactin A and/or macrolactin A.

TABLE 2

| Property | Macrolactin A | 7-O-malonyl-macrolactin A | 7-O-succinyl-macrolactin A |
|---|---|---|---|
| Molecular formula | $C_{24}H_{35}O_5$ | $C_{27}H_{36}O_8$ | $C_{28}H_{38}O_8$ |
| Molecular weight | 402.53 | 488.57 | 502.60 |
| UV (MeOH) | 227 (4.537) | 227 (4.397), 230 (sh) | 227 (4.596) |
| $[\lambda_{max}$ (lg ε)] | 261 (4.146) | 260 (4.006) | 259 (4.192) |
| $[\alpha]^{22D}$ (c in MeOH) | −10.7 (0.68) | −6.2 (0.63) | −19.9 (0.7) |
| (−)-MS-ESI-TOF [m/z (%)] | 401.2 (38) [M − H]$^−$ | 487.2 (100) [M − H]$^−$ | 501.3 (100) [M − H]$^−$ |
| | 437.2 (100) [M + Cl]$^−$ | 443.2 (44) [M − H—CO$_2$]$^−$ | 117.0 (12) |
| | 803.4 (63) [2M − H]$^−$ | 383.2 (27) [M-H − Malonic acid]$^−$ | [Bernstein acid − H]$^−$ |

Described in the following examples is a fermentative production method employing a shake culture. Other prior art submersion processes in fermenters can also be employed for large-volume cultivation. This includes batch, fed batch and continuous fermentation processes.

The invention will next be described in greater detail with the aid of examples. The figures show the following:

Figure 2:
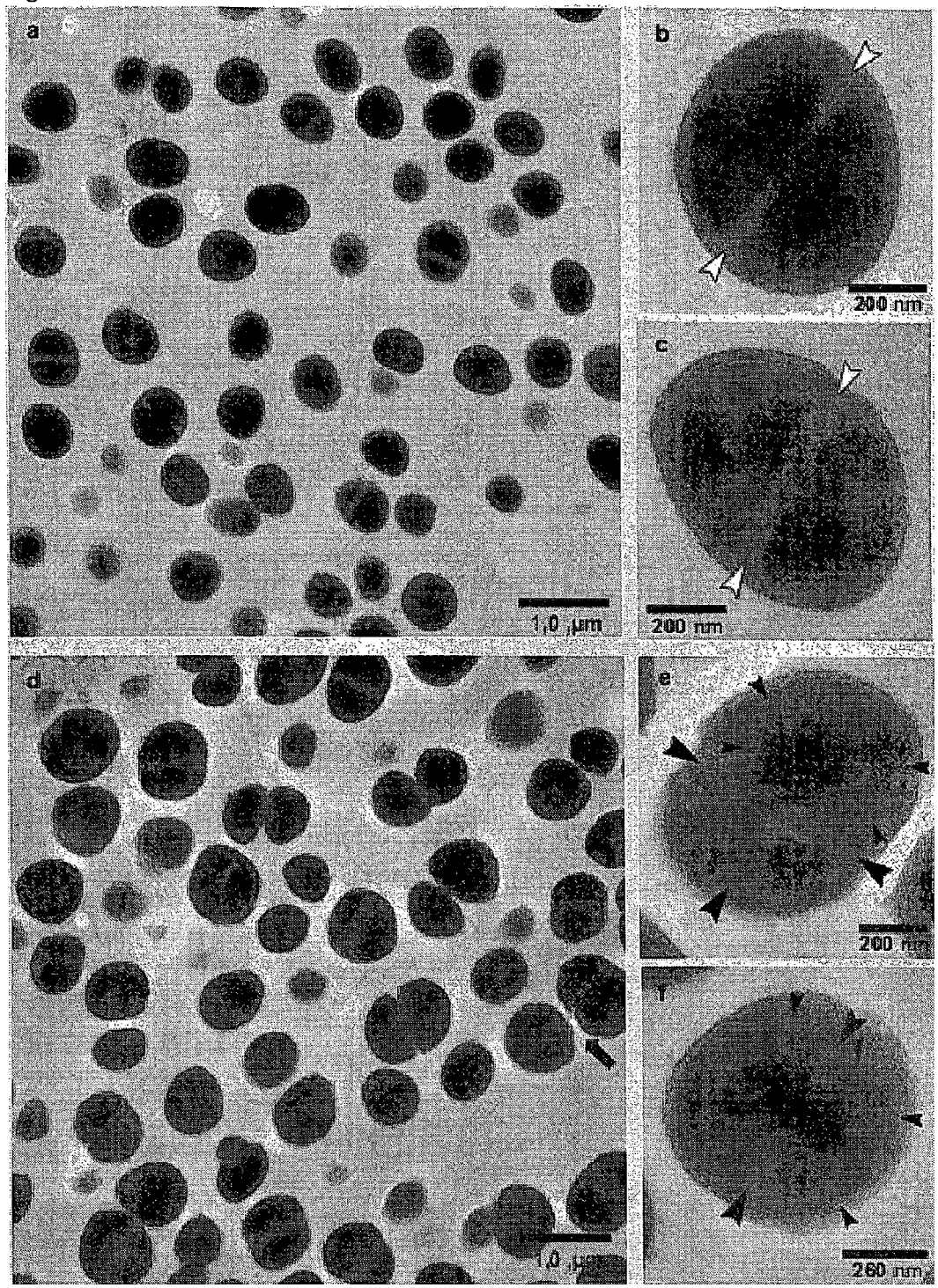
Figure 3:
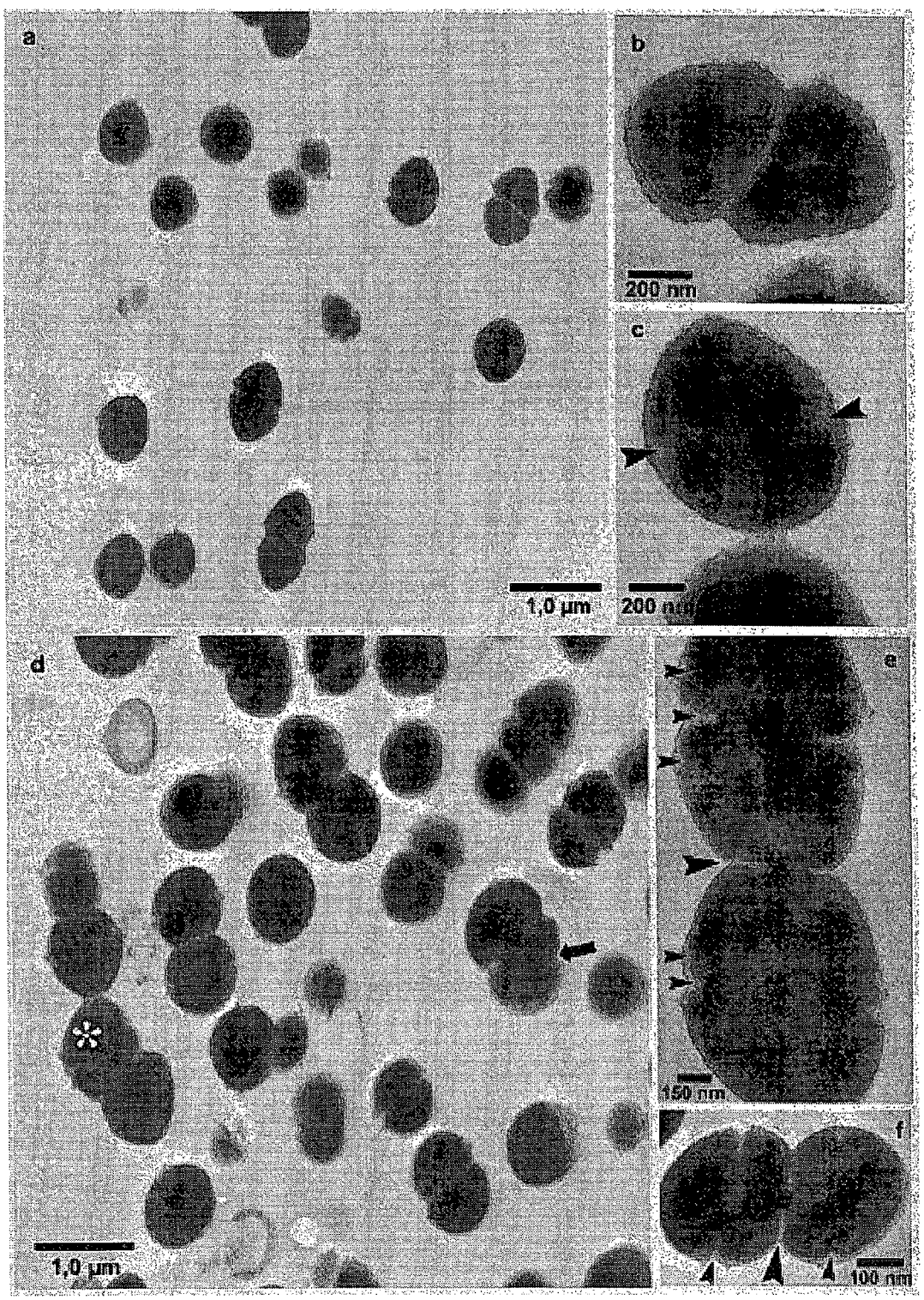
Figure 4:
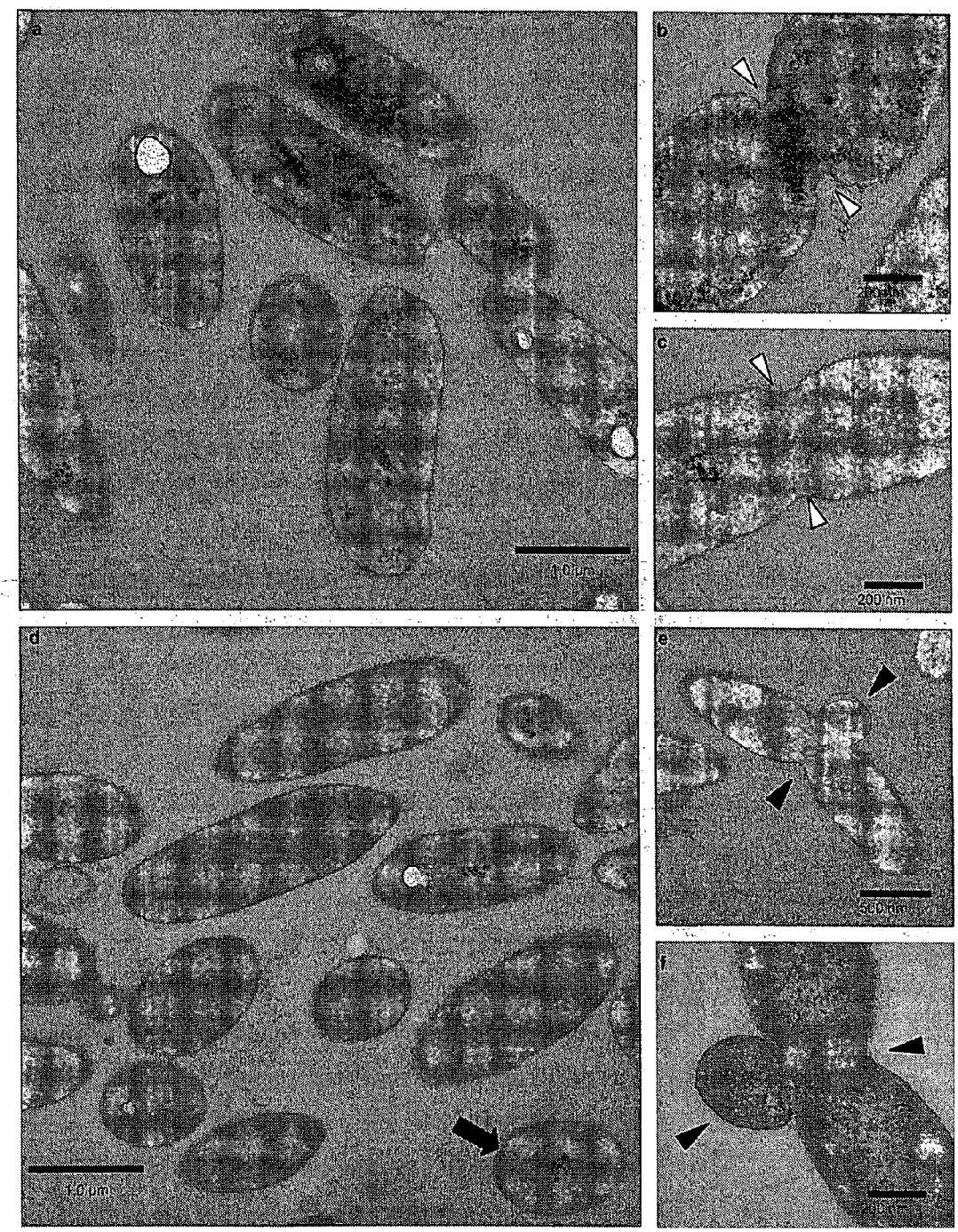
Figure 5:
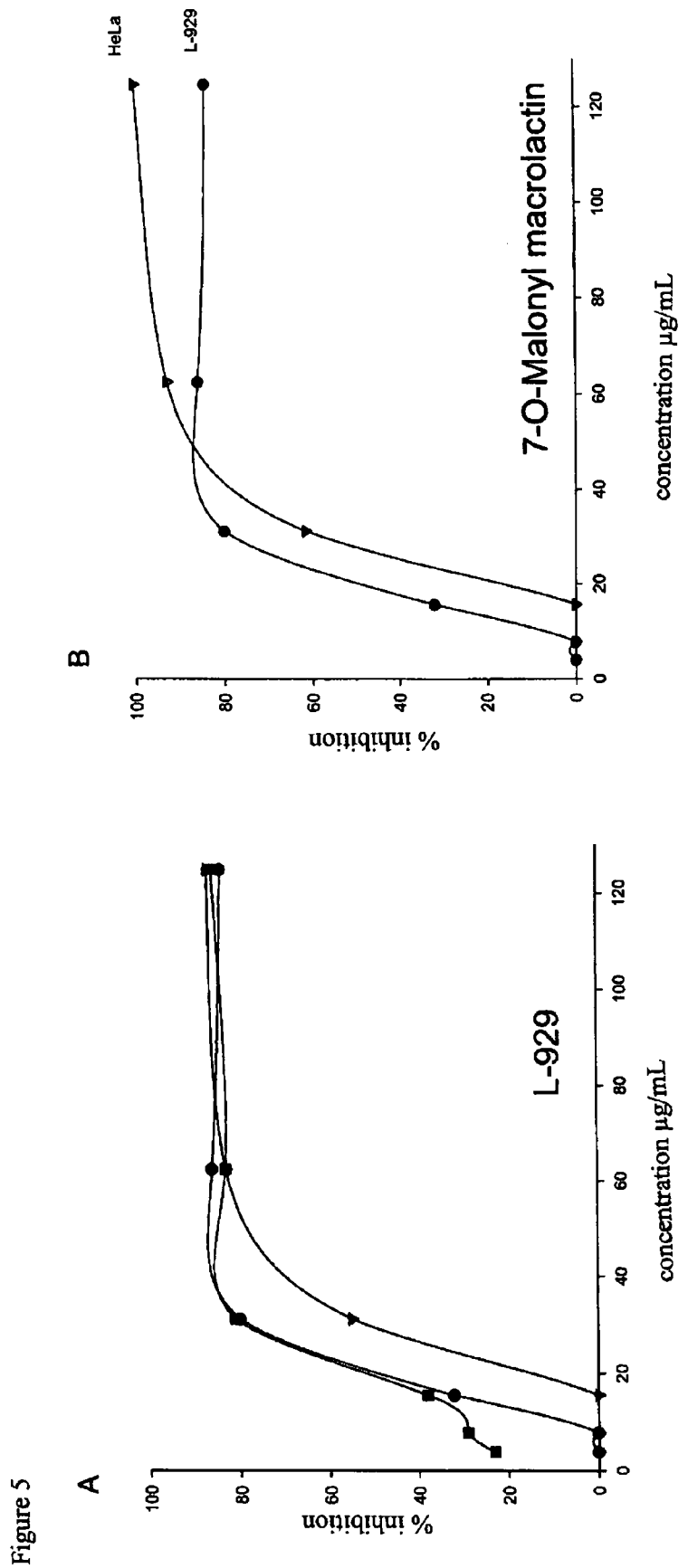

FIGS. 2 a), b) and c) are electron microscope photographs of *S. aureus* MRSA 3 after 4 hours growth without antibiotic and d), e) and f) in the presence of 16 μg/ml 7-O-malonyl macrolactin A;

FIG. 3 a) to c) are electron microscope photographs of *E. faecium* VRAR E315 after 4 hours growth without antibiotic and d), e) and f) in the presence of 16 μg/ml 7-O-malonyl macrolactin A;

FIG. 4 a) to c) are electron microscope photographs of *Burkholderia cepacia* SCV after 4 hours growth without antibiotic and d), e) and f) in the presence of 128 μg/ml 7-O-malonyl macrolactin A;

FIG. 5A shows the inhibition of the proliferation of mouse cells L-929 by means of 7-O-malonyl macrolactin A (●), 7-O-succinyl macrolactin A (▼) and macrolactin A (■), and;

FIG. 5B shows the inhibition of the proliferation of human epithelial cells (HeLa, ▼) and mouse cells L-929 (●) by means of 7-O-malonyl macrolactin A.

EXAMPLE 1

Cultivation of *Bacillus subtilis* for the Production of 7-O-Malonyl Macrolactin A Producer strain DSM 16696 was injected into a liquid culture medium comprising 5 g/l yeast extract, 20 g/l tryptone, 5 g/l sodium chloride and 5 g/l glucose at a pH of 7. Present in the culture medium during cultivation in a shake culture (120 Upm) for more than 7 days at 30° C. was 4% by weight of the hydrophobic adsorbent resin Amberlite XAD-16 (Röhm und Haas, Germany).

Following extraction by decanting, the adsorbent resin was washed in a column containing 50% aqueous methanol, the adsorbed compounds were next eluted with methanol and then concentrated by means of evaporation in a rotary evaporator to 1/100 of the culture volume. The methanol was removed from the extract by means of evaporation, and the residual aqueous mixture extracted 4 times with the aid of ethyl acetate. The ethyl acetate was removed under reduced pressure yielding approx. 300 mg of oily residue from a total culture of 4 l, to which the adsorbent resin had been added. Said residue was re-suspended in methanol, and the solution extracted 4 times with the same volume of n-heptane to remove lipophilic products and contaminants.

EXAMPLE 2

Cultivation of *Bacillus subtilis* for the Production of 7-O-Malonyl Macrolactin A For production purposes, the producer strain was used to inoculate a medium OM, which, having a pH of 7, is advantageous for the production of macrolactins, since employment of the same process sequence yielded an isolate of greater purity.

OM medium is obtained by autoclaving 1.0 g starch, 1.0 g glucose, 1.0 g peptone and 1.5 g yeast extract per 980 ml water and by adding 10 ml/l solution A (5 g/l $KH_2PO_4$, 5 g/l $K_2HPO_4$, autoclaved), 10 ml/l solution B (17 g/l $MgSO_4$, 1.0 g/l NaCl, 0.7 g/l $MnSO_4$, 0.06 g/l $CuSO_4$, autoclaved), 1 ml/l solution C (7 g/l $FeSO_4.7H_2O$, 22 g/l $Na_3$-citrate.$3H_2O$, 2.0 g/l ammonium citrate, 7.5 g/l Na-thioglycalase, 33 g/l Na2-succinate.$6H_2O$, sterile-filtered) and 1 ml/l solution D (100 mg/l biotin, 350 mg/l nicotinic acid amide, 300 mg/l thiamine.HCl, 200 mg/l p-amino benzoic acid, 100 mg/l pyridoxal hydrochloride, 100 mg/l Ca-panthothenate, 50 mg/l vitamin $B_{12}$, sterile filtered).

EXAMPLE 3

Purification of Macrolactins by Means of Liquid Chromatography

Extracts and fractions from examples 1 and 2 were analyzed by means of reversed-phase liquid chromatography (RP-HPLC) using a Nucleosil 100-5 C18 column (125/2 mm, Macherey Nagel). Used for detection were a 320-600 nm UV-diode array detector and an external light scatter detector (PL•ELS-1000, Polymer Laboratories). Employed as solvents were A: 0.5% acetic acid/water and B: 0.5% acetic acid/methanol at a flow rate of 0.3 ml/min. The macrolactins were separated by means of preparatory RP-HPLC using a Nucleosil 100-7 C18 column (250/21 mm, Macherey-Nagel) and a 51% to 56% gradient of solvent A and solvent B at a flow rate of 30 ml/min, with UV detection at 280 nm. Between 40 and 60 mg extract in 0.2 ml methanol was used for injection purposes.

The purification of macrolactins was accomplished in the following manner: preparatory RP-HPLC was employed using a Nucleosil 100-7 C18 column (250/21 mm, Macherey-Nagel, Düren, Germany) with the following solvent gradients: solvent A (0.5% acetic acid/51% aqueous methanol) and solvent B (0.5% acetic acid/56% aqueous methanol): solvent B from 0 to 100% for over 60 minutes at a flow rate of 30 ml/min. UV detection was at 280 nm. 40 to 60 mg extract in 0.2 ml methanol was used for injection. Each of the macrolactins (5 to 7 mg) was then purified using chromatography in a LH-20 column (760/25 mm, the solvent used being methanol/dichloromethane (1:1) at a flow rate of 5 ml/min.) with an application quantity of between 5 and 7 mg.

Between 4 and 6 mg macrolactin A, 5 and 7 mg 7-O-malonyl macrolactin A and 6 and 8 mg 7-O-succinyl macrolactin A were isolated from a 4 l culture using preparatory RP-HPLC and subsequent purification by means of LH-20 chromatography.

The macrolactin compounds isolated from the proposed *Bacillus subtilis* strain yielded the following data upon analysis: Macrolactin A, the molecular ion m/z at 402 and the UV absorptions at 227 and 261 nm enabled identification of the compound as macrolactin A or one of the 10E isomers thereof. The latter was ruled out by its optical rotation of $[\alpha]^{22}_D = -138$, compared to a result of $-10$ for macrolactin A. A comparison of the $^1$H and $^{13}$C-NMR data for the well-defined spectra of macrolactin A in methanol $d_4$ are shown in Table 2. The signals were identified by means of $^1$H, $^1$H-COSY and $^1$H—, $^{13}$C-HMBQ spectra.

EXAMPLE 4

Antimicrobial Effect

The agar diffusion method employing Mueller-Hinton (MH) agar (Difco Laboratories) was used to determine effectiveness against bacteria and yeasts. Sterile paper disks (Schleicher & Schüell, Germany) were seeded with 10 µl crude extract or with a solution of purified macrolactin (final compound concentration on the disk 50 µg) and then placed on the surface of MH-agar plates that had been seeded beforehand with a suspension of overnight culture of the test microorganisms at a concentration of $10^5$ cells/ml. Following incubation for 18 hours at 37° C., the diameter of the zones of inhibition of growth around the disks was measured.

The crude extract of Example 1 exhibited full bactericidal activity with a completely clear aureola about the disk. It is thought that this result arises from the cumulative action of the macrolactins so isolated.

7-O-malonyl macrolactin A exhibited antibacterial activity against gram-positive bacteria, such as, for example, *Burkholderia cepacia*, gram-negative reference and clinical isolates with an effectiveness comparable to or better than that obtainable with erythromycin. A notable advantage conferred by the novel capabilities of 7-O-malonyl macrolactin A and 7-O-succinyl macrolactin A, in particular against methicillin or ampicillin, vancomycin and/or erythromycin-resistant bacterial isolates is that said compounds also exhibit antibacterial activity against antibiotic-resistant isolates. The findings are set out in Table 3 hereunder:

TABLE 3

Comparison of the antibacterial activity in vitro of macrolactins and conventional antibiotics

| Test strain | Inhibition zone (mm) | | | | | | |
| --- | --- | --- | --- | --- | --- | --- | --- |
| | Crude Extract | Macro-lactin A | 7-O-Malonyl-macrolactin A | 7-O-Succinyl-macrolactin A | Erythro-mycin | Vanco-mycin | Ampi-cillin |
| *S. aureus* DSMZ 1104** | 28 | 18 | 26 | 18 | 30 | 20 | 30 |
| *S. aureus***,# | 32 | 25 | 30 | 22 | 40 | 27 | 41 |
| MRSA 2 | 24 | 27 | 40 | 37 | 0 | 24 | 0 |
| MRSA 3 | 28 | 35 | 41 | 38 | 0 | 24 | 0 |
| *E. faecalis* ATCC 29212 | 18 | 0 | 25 | 12 | 25 | 24 | 32 |
| *E. faecalis* VRAS E305 | 15 | 0 | 15 | 0 | 0 | 0 | 35 |
| *E. faecium* VRAR E315 | 40 | 0 | 15 | 20 | 25 | 0 | 0 |
| *B. cepacia* SCV* 141 | 40 | 0 | 15 | 0 | 0 | not determined | 0 |

*SCV = Small Colony Variant
MRSA = Methicillin-resistant *S. aureus*
VRAS = Vancomycin-resistant, ampicillin-sensitive
VRAR = Vancomycin-resistant, ampicillin-resistant
**= Control strains, methicillin-sensitive
= own collection
10 µl crude extract and 50 µg macrolactin were spread on a disk. 78 µg erythromycin, 30 µg vancomycin and 10 µg ampicillin were contained on a disk (prepared disks).

The data shown in Table 3 indicate that 7-O-succinyl macrolactin A exhibits no activity against, for example, the erythromycin-resistant strains *E. faecalis* VRAS E305 and *B. cepacia* SCV* 141 but that only 7-O-malonyl macrolactin A produced an inhibition zone due to antibacterial activity.

By contrast, both 7-O-succinyl macrolactin A and 7-O-malonyl macrolactin A exhibit antibacterial activity against the multiresistant enterococci, as is indicated, for example, at staphylococci MRSA 2 and MRSA. In contrast to the macrolactin A, which also exhibits activity, 7-O-succinyl macrolactin A and 7-O-malonyl macrolactin A have, when applied as proposed, the advantage of having low cytotoxicity, a property that renders these compounds in the low concentration region of the MBC suitable for use as antibacterial ingredients, and especially as bacteriostatic ingredients.

The data shown in Table 3 also suggest that 7-O-malonyl macrolactin A has markedly stronger antibacterial activity against all test bacteria compared to macrolactin A. The sole exception is *E. faecium* VRAR E315, against which the antibacterial activity of 7-O-malonyl macrolactin A is slightly weaker than that of 7-O-succinyl macrolactin A. It is therefore preferred, in one embodiment of the invention, that the antibacterially active pharmaceutical composition comprise 7-O-malonyl macrolactin A, optionally in combination with 7-O-succinyl macrolactin A.

The proposed compound 7-O-malonyl macrolactin A, in particular, demonstrated capability to inhibit the growth of methicillin-resistant *Staphylococcus aureus* (MRSA 2 or 3, clinical isolate) and vancomycin-resistant *Enterococcus* (VRE). 7-O-malonyl macrolactin A was the most active of the three macrolactin compounds produced from the proposed *Bacillus subtilis* strain. Use of the agar diffusion procedure permitted observation of a broad aureola of bacterial growth inhibition around the disk. Inhibition of the bacterial growth of *Staphylococcus* was, however, incomplete, and small colonies were evident within this zone.

The *B. cepacia* strain used, which is a clinical isolate from a cystic fibrosis patient, forms small colonies (SCV 141). This isolate exhibits the typical characteristics of bacteria in combination with mucoidal bacteria in a biofilm and which, due to higher antibiotic resistance, has considerable clinical relevance for cystic fibrosis patients in particular. In this comparison test, 7-O-malonyl macrolactin A alone exhibited antibacterial activity against the isolate of *B. cepacia*, in tandem with characteristics that suit it to medical application.

EXAMPLE 5

Minimal Inhibition Concentrations of 7-O-Malonyl Macrolactin A

Although the minimal inhibition concentrations (MIC) of 7-O-malonyl macrolactin A for staphylococci was greater than 128 µg/ml, concentrations of between 1 and 4 µg/ml permitted pronounced inhibition of bacterial growth for the reference strain (*S. aureus* #, non-methicillin-resistant), or rather, for the MRSA strains. The MIC value for 7-O-malonyl macrolactin A against *Enterococcus faecalis* ATCC 29212 exceeded 128 µg/ml and bacterial growth was markedly inhibited at the sub-MIC value of 4 µg/ml. 7-O-malonyl macrolactin A, although exhibiting activity at MIC values above 128 µg/ml against VRE strains, noticeably inhibited bacterial growth at 0.06 or 4 µg/ml for the strains *Enterococcus faecalis* E305, vancomycin-resistant/ampicillin-sensitive (VRAS) or rather, *Enterococcus faecium* B315, vancomycin-resistant/ampicillin-resistant (VRAR).

7-O-malonyl macrolactin A was not effective against some of the gram-negative bacteria tested by the inventors. Inhibition of the growth of clinical isolates of gram-negative bacteria was observed, e.g. for *Burkholderia cepacia* SCV 141 at concentrations of 32 µg/ml, however, such activity was not observed against wild-type strain *Burkholderia cepacia* 139, for which the MIC value exceeded 128 µg/ml. These results indicate, however, that due to its effectiveness even against clinically relevant gram-negative strains, in particular those having resistance to at least one antibiotic, 7-O-malonyl macrolactin A is suitable for medical purposes.

Inhibition activity against *Candida* spp. was also noted.

The marked inhibition of bacterial growth, which was observed at sub-MIC concentrations of 7-O-malonyl macrolactin A, indicates that this compound, even at very low concentrations, is bacteriostatically active against at least some of the test strains.

Even comparing the antimicrobial activity of 7-O-malonyl macrolactin A with that of reference compounds in liquid culture suggests that the minimal required bacteriostatic concentrations (MBC) at which pronounced inhibition of bacterial growth was observed, was very low for 7-O-malonyl macrolactin A.

TABLE 4

Antimicrobial activity of 7-O-malonyl macrolactin A and reference compounds against clinical isolates and reference strains

| Strain | 7-O-malonyl-macrolactin A | | Vanco-mycin | Ampi-cillin | Erythro-mycin | Genta-mycin | MCZ |
|---|---|---|---|---|---|---|---|
| | MIC | MBC | | | MIC | | |
| *S. aureus*\*\*,# | >128 | 1 | 0.125 | 0.06 | 0.06 | 0.25 | ND |
| MRSA 2 | >128 | 4 | 2 | >128 | >128 | 128 | ND |
| MRSA 3 | >128 | 4 | 1 | 64 | >128 | 128 | ND |
| *E. faecalis* ATCC 29212 | 128 | 4 | 2 | 0.5 | 2 | 32 | ND |
| *E. faecalis* VRAS E305 | >128 | 0.06 | >128 | 0.5 | 128 | 64 | ND |
| *E. faecium* VRAR E315 | >128 | 4 | >128 | >128 | 2 | 64 | ND |
| *B. cepacia* WT139 | >128 | — | ND | >128 | >128 | >128 | ND |
| *B. cepacia* SCV 141 | 128 | 32 | ND | 128 | 128 | >128 | ND |
| *Candida parapsilosis* DSM5784 | 128 | — | ND | ND | ND | ND | 2 |
| *Candida krusei* DSM 6128 | >128 | 32 | ND | ND | ND | ND | 2 |
| *Candida albicans* DSM 11225 | >128 | — | ND | ND | ND | ND | 2 |

Concentrations are expressed in µg/ml.
ND = not determined
MIC = minimal inhibitory concentration
MBC = minimal bacteriostatic or fungistatic concentration
MCZ = miconazol, which is a fungicide The data given in Table 4 suggest that 7-O-malonyl macrolactin A, at low concentrations is active in the same order of magnitude, as prior art antibiotics. This suggests that it is not necessary that the concentration of 7-O-malonyl macrolactin A be at MIC, although it is necessary that the minimal bacteriostatic concentration be reached for strong bacteriostatic activity to occur. 7-O-malonyl macrolactin A exhibits, moreover, activity against pathogenic yeasts, an example whereof is *Candida*.

EXAMPLE 6

Biocidal Activity of 7-O-Malonyl Macrolactin A Against Pro- and Eukaryotic Microorganisms Investigation of the bacteriostatic activity of 7-O-malonyl macrolactin A required testing the effects of sub-MIC concentrations. The kinetics of growth for *Staphylococcus aureus* (#), shown in FIG. 1A, indicates that 7-O-malonyl macrolactin A kills off this bacterium within the first 4 hours following dosage, even at concentrations far below the MIC. The subsequent cultivation time indicates that the growth of this bacterium is reduced by a factor of 10. The activity of 7-O-malonyl macrolactin A against MRSA 3 (FIG. 1B) becomes apparent only following prolonged cultivation, even though the growth of this bacterium strain after 4 hours is almost completely inhibited. 24 hours after treatment, the titre of viable cells was reduced by a factor of 100 as compared to the control without 7-O-malonyl macrolactin A.

Figure 1:
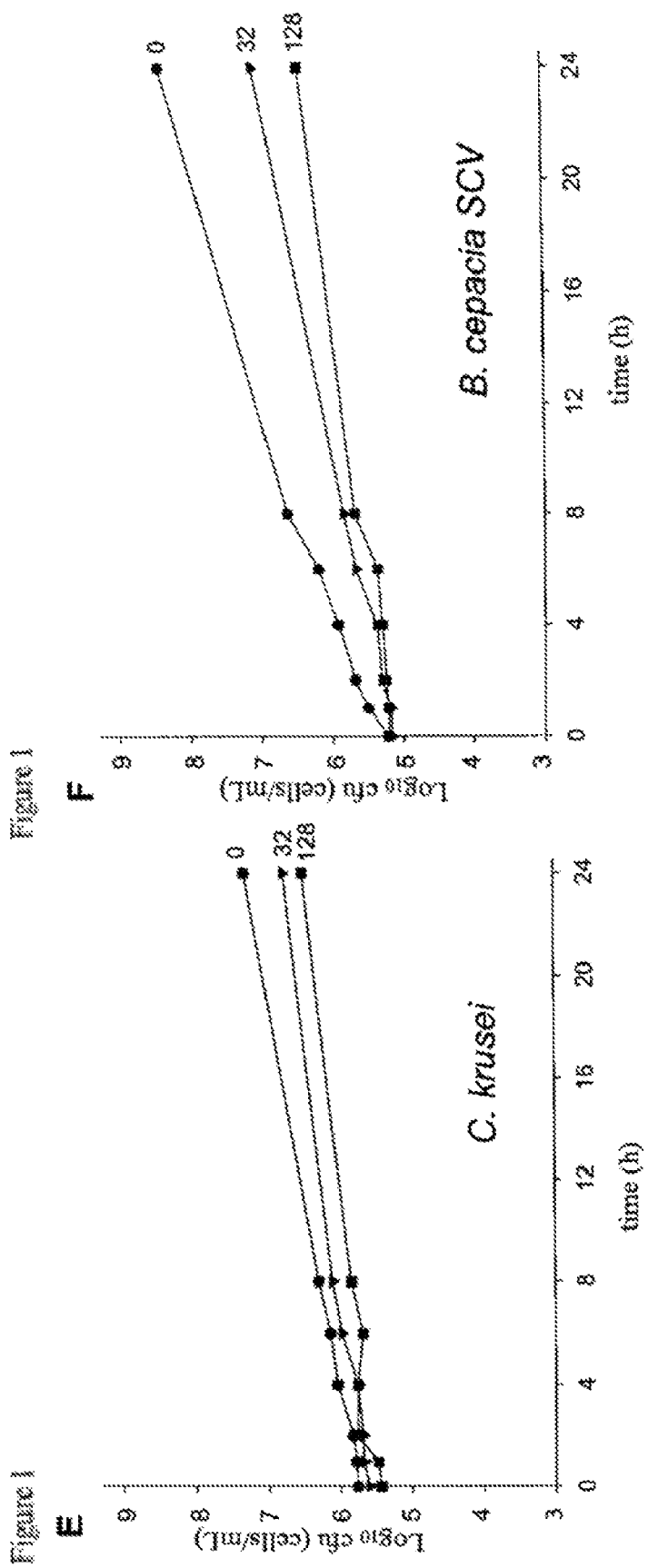
FIG. 1A shows the kinetics of growth for *Staphylococcus aureus* (#) without (0) and with 1 μg/ml (1) or 4 μg/ml (4) 7-O-malonyl macrolactin A.
FIG. 1B shows the kinetics of growth for *Staphylococcus aureus* (methicillin-resistant, from a clinical isolate, MRSA 3) without (0) and with 1 μg/ml (1) or rather, 4 μg/ml (4) 7-O-malonyl macrolactin A.
FIG. 1C shows the kinetics of growth for *Enterococcus faecalis* ATCC 29212 without (0) and with 4 μg/ml (4) or rather, 16 μg/ml (16) 7-O-malonyl macrolactin A.
FIG. 1D shows the kinetics of growth for *Enterococcus faecium* (VRAR E315, vancomycin-resistant, ampicillin-resistant, clinical isolate) without (0) and with 4 μg/ml (4) or rather, 16 μg/ml (16) 7-O-malonyl macrolactin A.
FIG. 1E shows the kinetics of growth for *Candida krusei* DSMZ6128 without (0) and with 32 μg/ml (32) or rather, 128 μg/ml (128) 7-O-malonyl macrolactin A.
FIG. 1F shows the kinetics of growth for *Burkholderia cepacia* SCV 141 (clinical isolate) without (0) and with 32 μg/ml (32) or rather, 128 μg/ml (128) 7-O-malonyl macrolactin A.

Four hours following cultivation, 7-O-malonyl macrolactin A inhibited the growth of *Enterococcus faecalis* ATCC 29212; in this case, the titre of viable cells remained below that of the untreated control culture throughout the final phase of the cultivation period (FIG. 1C).

Four hours following cultivation in the presence of 7-O-malonyl macrolactin A, the growth of *Enterococcus faecium* E315, (vancomycin-resistant, ampicillin-resistant), was almost completely inhibited (FIG. 1D).

It is interesting to note that 7-O-malonyl macrolactin A exhibits stronger bacteriostatic activity against antibiotic-resistant strains isolated from clinical patients than against non-resistant strains. It was also observed that the live cell count did not rise substantially during cultivation in the presence of 7-O-malonyl macrolactin A. Particularly interesting is a comparison of FIG. 1A with FIG. 2B, which clearly indicates that the bacteriological activity of 7-O-malonyl macrolactin A against the antibiotic-resistant MRSA 3 is of a magnitude equal to or greater than the activity against reference strain *S. aureus*[#], which is not antibiotic resistant.

7-O-malonyl macrolactin A exhibits antibiotic activity even against the eukaryotic microorganism *Candida krusei* (FIG. 1E) and against *Burkholderia cepacia* SCV 141 (FIG. 1F) which, in and of itself, is resistant to prior art antibiotics and inhibits growth up to a factor of 10 at concentration of 128 µg/ml for *C. krusei* and 32 µg/ml for *B. cepacia*.

In general, investigations of the inhibitory activity of 7-O-malonyl macrolactin A did not indicate dosage dependency where two sub-MIC concentrations were used in experiments.

EXAMPLE 7

Disruption of Cell Division of Bacteria by Means of 7-O-Malonyl Macrolactin A

Investigation of bacterial strains from clinical isolates which, in accordance with Example 5, in shake cultures are in the presence of sub-MIC concentrations of 7-O-malonyl macrolactin A and undergo pronounced growth inhibition, indicates that 7-O-malonyl macrolactin A interferes with the process of cell division. It is thought that 7-O-malonyl macrolactin A inhibits the division of bacterial cells, which interrupts the proliferation thereof. This investigation suggests that 7-O-malonyl macrolactin A is more effective in this role than the prior art 7-O-succinyl macrolactin A or macrolactin A.

The antibiotic activity of 7-O-malonyl macrolactin A becomes apparent at concentrations far below the MIC, which suggests that use of sub-MIC dosages may provide effective concentrations for medical purposes. In particular, in combination with the weakly cytotoxic activity of 7-O-malonyl macrolactin A, primarily at low concentrations, this property confers the advantages of achieving antibiotic effect at low dosages.

Electron microscope photographs of the clinical isolate of *Staphylococcus aureus* (MRSA 3, methicillin-resistant) in FIG. 2 illustrate the activity of 7-O-malonyl macrolactin A. FIGS. 2a) to c) show untreated shake cultures following incubation for 4 hours and FIGS. 2d) to f) show the same cultures but with the addition of 16 µg/ml 7-O-malonyl macrolactin A. This concentration, although clearly sub-MIC, strongly inhibits growth, which can also be observed in FIG. 1B for concentrations of 1 and 4 µg/ml. 7-O-malonyl macrolactin A influences cell division in MRSA 3, which is evident from the altered division planes. The untreated cells shown in FIGS. 2a) to c) exhibit division planes that appear as a light-shaded transverse wall as indicated in FIGS. 2b) and c) by the white arrowheads. The treated MRSA 3, on the other hand, exhibits disrupted cell division. The large black arrowheads (FIGS. 2e) and f)) indicate the division planes, while the small black arrowheads indicate an asymmetrical initiation of cell division.

The effect of 7-O-malonyl macrolactin A on cell division can also be observed from the electron microscope photographs of *Enterococcus faecium* (VRAR=vancomycin-resistant, ampicillin-resistant, E315, clinical isolate) shown in FIG. 3. The division planes of the untreated cells after 4 hours growth without antibiotic appear as light regions in FIGS. 3a), b) and c). In FIGS. 3d) to f), which show initiations with 16 µg/ml 7-O-malonyl macrolactin A, there are no fully formed division planes evident, but anomalous, asymmetrical cell division is being initiated (indicated by large black arrowheads). In this example, however, no fully formed cell division planes are evident. The initiation of asymmetrical cell division is indicated by the small black arrowheads. One visible result of disrupted cell division (FIG. 3f), is a pseudo-multicellular chain (indicated by a white star in FIG. 3d), which also does not exhibit a complete septum in the plane and in which, in the case of the untreated cells (FIGS. 3a) and b)), the cell division is visible as a light-shaded region.

The electron microscope photographs moreover elucidate the bacteriostatic effect of 7-O-malonyl macrolactin A against gram-negative bacteria, an example whereof is the cell division of *Burkholderia cepacia*. Thus, FIGS. 4a, b and c show *Burkholderia cepacia* SCV (clinical isolate) in a shake culture without the addition of antibiotic ingredients (control) and FIGS. 4d, e and f after 4 hours growth in a shake culture in the presence of 128 µg/ml 7-O-malonyl macrolactin A. In the control culture, white arrowheads point to the cell division planes and the transverse walls in connection therewith. In the case of the gram-negative cells treated with 7-O-malonyl macrolactin A, (FIGS. 4e and f) black arrows indicate the cell division planes and the unnatural protuberances. In the case of the cells treated with 7-O-malonyl macrolactin A, anomalously sized cells were also evident, as indicated in FIG. 4d by a black arrow.

EXAMPLE 8

Activity of 7-O-Malonyl Macrolactin A Against Microorganisms, Especially Against Gram-Negative Bacteria and Eukaryotic Microorganisms In one example of its activity against eukaryotic microorganisms, e.g. yeast, 7-O-malonyl macrolactin A was tested against *Candida krusei* DSMZ 6128. The results, shown in FIG. 2e, indicate some inhibitory activity. 7-O-malonyl macrolactin A also exhibits inhibitory activity against the gram-negative bacterium *Burkholderia cepacia* SCV 141 (FIG. 2f).

EXAMPLE 9

Cytotoxic Activity of 7-O-Malonyl Macrolactin A, 7-O-Succinyl Macrolactin A and Macrolactin A Against Animal Cells The cytotoxicity of 7-O-malonyl macrolactin A was compared to that of 7-O-succinyl macrolactin A and macrolactin A in vitro with respect to the inhibition of the proliferation of L929 mouse fibroblast cells or the human epithelial cell line HeLa.

For the cell culture, the HeLa cells were cultivated in low-glucose DMEM medium (Gibco), and the L929 cells in high-glucose DMEM medium. Both were supplemented with 10% by volume foetal calf serum (Gibco) at 37° C. in an atmosphere containing 5% $CO_2$. The cells were extracted from stock cultures by means of trypsinization with EDTA (HeLa) or without EDTA (L929), then counted and diluted to $2\times10^5$ cells/ml. For the tests, microtitre plates (Nunc.) comprising 96 depressions were plated out in serial dilution without or in the presence of the test compounds or methanol. Determination of morphological alterations of the cells was carried out by means of phase contrast microscopy after 1, 2 and 5 days incubation.

After 5 days cultivation, cell counts were determined by the CyQUANT cell proliferation test (Molecular Probes), which is a highly sensitive microtitre plate test based on fluorescence. The test employs the dye CyQUANT, which, by binding to cellular nucleic acids, enhances fluorescence, which can then be measured by fluorescein excitation. The emission of fluorescence by the dye-nucleic acid complex correlated linearly with the cell count. For test purposes, the residue was carefully removed after 5 days incubation, the cells washed with PBS (phosphate buffered saline solution), the buffer removed and the cells frozen at −80° C. For the test, the cells were thawed at ambient temperature and lysated in a buffered solution containing the dye CyQUANT, in accordance with manufacturer's instructions. Fluorescence was measured by means of a fluormetric microtitre-plate reader (Titertex Fluorskan II) (excitation at 480 nm, emission at 520 nm). The absorption values were used to calculate the percentage of cellular proliferation in medium both alone and in the presence of serial dilutions of methanol and the macrolactin compounds. As illustrated in FIG. 5A or 5B, after a cell count of ca. $10^4$–$2\times10^5$/ml had been reached, the DMEM medium was replaced by fresh medium, containing concentrations of 7-O-malonyl macrolactin A or, as shown in Table 5, of various macrolactins. Proliferation was measured by means of the fluorescence-based test CyQUANT for determining viable cell counts. Table 5 illustrates the relative inhibition of proliferation as compared to a control culture comprising fresh medium without the addition of a macrolactin.

TABLE 5

Inhibition of proliferation by means of macrolactins

| Compound | Cells | Compound concentration µg/ml | | | | | |
|---|---|---|---|---|---|---|---|
| | | 125 | 56.5 | 31.25 | 15.6 | 7.8 | 3.9 |
| 7-O-malonyl macrolactin A | HeLa | 100% | 93% | 62% | 0 | 0 | 0 |
| 7-O-malonyl macrolactin A | L929 | 84% | 86% | 80% | 32% | 0 | 0 |
| 7-O-succinyl macrolactin A | L929 | 87% | 83% | 55% | 0 | 0 | 0 |
| 7-O-macrolactin A | L929 | 83% | 83% | 81% | 38% | 29% | 23% |

FIG. 5A clearly shows that macrolactin A (■), like 7-O-succinyl macrolactin A (▼), more strongly inhibits the proliferation of mouse cells L292 than 7-O-malonyl macrolactin A (●).

FIG. 5B shows that the proliferation of human cells, shown here in the example of HeLa cells (▼), is inhibited to a lesser extent by 7-O-malonyl macrolactin A than that of mouse fibroblast cells L-929 (●). It is interesting that, at low concentrations, inhibition of the proliferation of human cells is weaker than that of mouse cells. At higher concentrations, however, 7-O-malonyl macrolactin A was cytotoxic for both the human epithelial test cells and the fibroblast cells.

It has already been demonstrated that macrolactin A, in addition to its antibacterial capability, exhibits cytotoxic and antiviral activity. The proposed isolated 7-O-malonyl macrolactin A at higher concentrations exhibits higher cytotoxicity than the other reference test compounds.

At a concentration of 15.6 µg/ml, 7-O-malonyl macrolactin A failed to inhibit the proliferation of HeLa cells. However, the fibroblast cell line was approx. 32% inhibited at the same concentration. Overall, 7-O-malonyl macrolactin A exhibits stronger inhibiting activity against the tested fibroblast cells than 7-O-succinyl macrolactin A, and for these two compounds no further inhibition activity was observed at a concentration of 7.8 µg/ml. Compared to macrolactin A, 7-O-malonyl macrolactin A at higher concentrations up to the test concentration of 15.6 µg/ml exhibited similar or slightly reduced inhibition activity against proliferation of the test fibroblast cells, but at concentrations of 7.8 and 3.9 µg/ml exhibited no further inhibition or proliferation as compared to macrolactin A.

Since the concentration levels above which cytotoxic activity becomes apparent for 7-O-malonyl macrolactin A exceed that at which marked bacteriostatic activity becomes evident, especially against antibiotic-resistant bacteria, 7-O-malonyl macrolactin A can be used in the production of pharmaceutical preparations for medical use. One notable advantage of 7-O-malonyl macrolactin A as compared to 7-O-succinyl macrolactin A or macrolactin A is its increased antimicrobial activity, especially at low concentrations, coupled with weak cytotoxicity against human cells, particularly in comparison with macrolactin A.

Microscopic investigation of the effect of 7-O-malonyl macrolactin A on human epithelial cells HeLa and the L929 mouse fibroblast cells revealed that the human cell line is subjected to less interference when treated with 7-O-malonyl macrolactin A than are those of the mouse. The antiproliferative activity is due to a toxic effect since the morphology of the treated cells was round. Proliferation of the control cells treated with methanol was not hindered.

Quantification of the cytotoxic effect of 7-O-malonyl macrolactin A using the CyQUANT test demonstrated that the compound was, at a concentration of 31.25 µg/ml, capable of inhibiting the proliferation of HeLa cells. The cells treated with a 62.5 µg/ml concentration of 7-O-malonyl macrolactin A exhibited practically complete inhibition of growth.

Translated Captions for the Figures

FIG. 1A y-axis: Log CFU (Colony Forming Units) Cells/ml
  x-axis: Time (HRS)
FIG. 1B y-axis: Log CFU (Colony Forming Units) Cells/ml
  x-axis: Time (HRS)
FIG. 1C: y-axis: Log CFU (Colony Forming Units) Cells/ml
  x-axis: Time (HRS)
FIG. 1D: y-axis: Log CFU (Colony Forming Units) Cells/ml
  x-axis: Time (HRS)
FIG. 1E: y-axis: Log CFU (Colony Forming Units) Cells/ml
  x-axis: Time (HRS)
FIG. 1F: y-axis: Log CFU (Colony Forming Units) Cells/ml
  x-axis: Time (HRS)
FIG. 5A: y-axis: % Inhibition
  x-axis Concentration µg/ml
FIG. 5B: y-axis: % Inhibition
  x-axis Concentration µg/ml

The invention claimed is:

1. Purified 7-O-malonyl macrolactin A.

2. A pharmaceutical composition comprising 7-O-malonyl macrolactin A according to claim 1.

3. The pharmaceutical composition of claim 2 for use against a bacterial infection.

4. The pharmaceutical composition of claim 3, wherein the infection is a bacterial infection, wherein the infecting bacterium has at least one resistance against another antibiotic compound.

5. The pharmaceutical composition of claim 4 wherein the other antibiotic compound is selected from the group comprising vancomycin, methicillin, ampicillin and erythromycin.

6. A pharmaceutical composition of claim 2, wherein the pharmaceutical composition is suitable for employing an effective concentration of 0.01 to 50 µg/ml.

* * * * *

UNITED STATES PATENT AND TRADEMARK OFFICE
CERTIFICATE OF CORRECTION

PATENT NO. : 7,977,375 B2
APPLICATION NO. : 11/663408
DATED : July 12, 2011
INVENTOR(S) : Kenneth N. Timmis et al.

It is certified that error appears in the above-identified patent and that said Letters Patent is hereby corrected as shown below:

Col. 4, line 23  Delete "(lg ϵ)=227 nm" and insert --(lg ε) = 227 nm-- therefor.

Cols. 3, 4, 5, 6 (Table 1)  Please delete the right half of the table under the heading "7-O-Malonyl macrolactin A" and replace it with the following table:

| 7-O-Malonylmacrolactin A | | | | | | |
|---|---|---|---|---|---|---|
| H | $\delta_H$ | m | $J$ [Hz] | C | $\delta_C$ | m |
| 1 | - | - | - | 1 | 167.94 | s |
| 2 | 5.59 | d | 11.7 | 2 | 118.52 | d |
| 3 | 6.67 | t | 11.3 | 3 | 144.50 | d |
| 4 | 7.25 | dd | 14.7, 11.7 | 4 | 130.79 | d |
| 5 | 6.15 | dt | 15.4, 7.2 | 5 | 140.51 | d |
| 6 | 2.60 | m | 5.3 | 6 | 40.13 | t |
| 7 | 5.50 | ddd | 6.0, 6.0, 6.0 | 7 | 74.72 | d |
| 8 | 5.75 | dd | 15.3, 5.5 | 8 | 132.06 | d |
| 9 | 6.71 | dd | 15.1, 11.3 | 9 | 128.09 | d |
| 10 | 6.13 | t | 10.2 | 10 | 130.91 | d |
| 11 | 5.63 | dt | 10.6, 8.4 | 11 | 129.78 | d |
| 12a | 2.63 | m | - | 12 | 36.39 | t |
| 12b | 2.33 | ddd | 13.0, 7.2, 5.5 | | | |
| 13 | 3.84 | ddd | 10.6, 6.0, 5.7 | 13 | 69.51 | d |
| 14 | 1.66 | m | - | 14 | 43.84 | t |
| 15 | 4.39 | dt | 6.3, 6.3 | 15 | 69.77 | d |
| 16 | 5.60 | dd | 15.1, 6.4 | 16 | 135.32 | d |
| 17 | 6.21 | dd | 15.1, 10.6 | 17 | 131.27 | d |
| 18 | 6.10 | dd | 15.1, 10.6 | 18 | 131.78 | d |
| 19 | 5.69 | ddd | 14.9, 7.0, 6.8 | 19 | 135.10 | d |
| 20a | 2.23 | td | 14.0, 6.8 | 20 | 33.03 | t |
| 20b | 2.15 | td | 14.4, 7.2 | | | |
| 21 | 1.54 | m | - | 21 | 25.81 | t |
| 22a | 1.70 | m | - | 22 | 36.08 | t |
| 22b | 1.62 | m | - | | | |
| 23 | 5.05 | ddq | 4.5, 7.1, 6.1 | 23 | 72.37 | d |
| 24 | 1.30 | d | 6.0 | 24 | 20.14 | q |
| 1' | - | - | - | 1' | 169.64 | s |
| 2' | 2.90 | m | - (br) | 2' | 44.74 | (a) |
| 3' | - | - | - | 3' | n.b. | |

Signed and Sealed this
Fourteenth Day of February, 2012

David J. Kappos
*Director of the United States Patent and Trademark Office*

CERTIFICATE OF CORRECTION (continued)
U.S. Pat. No. 7,977,375 B2

Col. 5, line 28  Delete "$\lambda_{max}$ (lg $\epsilon$)=227 nm" and insert --$\lambda_{max}$ (lg $\epsilon$) = 227 nm-- therefor.

Col. 5, line 40  Delete "$\lambda_{max}$ (lg $\epsilon$)=227 nm" and insert --$\lambda_{max}$ (lg $\epsilon$) = 227 nm-- therefor.

Col. 5, line 60  Delete " $[\alpha]^{22D}$ " and insert --$[\alpha]^{22}_{D}$-- therefor.
Table 2, left column Col. 8, line 23  Delete "$FeSO_4.7H_2O$" and insert --$FeSO_4 \cdot 7H_2O$-- therefor.

Col. 8, line 23  Delete "$Na_3$-citrate.$3H_2O$" and insert --$Na_3$-citrate$\cdot 3H_2O$-- therefor.

Col. 8, line 25  Delete "succinate.$6H_2O$" and insert --succinate$\cdot 6H_2O$-- therefor.

Col. 8, line 27  Delete "mine.HC1" and insert --mine·HC1-- therefor.

Col. 12, line 11  Delete "cepacia" and insert --*cepacia*-- therefor.

Col. 18, line 6  Delete "x-axis Concentration μg/ml"" and insert --x-axis: Concentration μg/ml-- therefor.

Col. 18, line 8  Delete "x-axis Concentration μg/ml"" and insert --x-axis: Concentration μg/ml-- therefor.